United States Patent [19]

Rutledge et al.

[11] 4,294,111
[45] Oct. 13, 1981

[54] PORTABLE FLUID INK TACK TESTER

[75] Inventors: Wyman C. Rutledge; J. Robert Graves, both of Chillicothe; William G. Cassill, McArthur, all of Ohio

[73] Assignee: The Mead Corporation, Dayton, Ohio

[21] Appl. No.: 119,052

[22] Filed: Feb. 6, 1980

[51] Int. Cl.³ .................................... G01N 19/04
[52] U.S. Cl. ........................... 73/150 R; 73/150 A
[58] Field of Search ................ 73/150 R, 150 A, 58

[56] References Cited

U.S. PATENT DOCUMENTS

| | | | |
|---|---|---|---|
| 1,960,226 | 5/1934 | Schoenberg | 73/60 |
| 2,101,322 | 12/1937 | Reed | 73/150 R |
| 2,762,219 | 9/1956 | Prentiss | 73/150 R |
| 3,186,221 | 6/1965 | Steib | 73/150 A |
| 3,531,986 | 10/1970 | van Gastel | 73/150 R |
| 3,901,069 | 8/1975 | van Gastel | 73/150 R |
| 3,901,149 | 8/1975 | Schulte-Kulkman | 73/150 R |

Primary Examiner—Gerald Goldberg
Assistant Examiner—Denis E. Corr
Attorney, Agent, or Firm—Stephen H. Cagle; Charles N. Shane; Wilson G. Palmer

[57] ABSTRACT

A manually portable fluid ink tack tester (10) for sampling and testing the tack of printing inks during press runs has two engaged, rotating rolls (25,26) mounted on parallel axes and in rolling contact on the tester frame (15). One (26) is extended outwardly from the frame (15) to expose the surface of the roll for contacting an ink coated surface and receiving an ink sample therefrom. After receiving the ink, the tester (10) is removed from the ink coated surface and a motor (35) in the tester (10) rotates the rolls (25,26). The force necessary to split the ink between the two rolls (25,26) is measured (13,40) and displayed (13,48), giving an indication of the tack of the ink.

4 Claims, 8 Drawing Figures

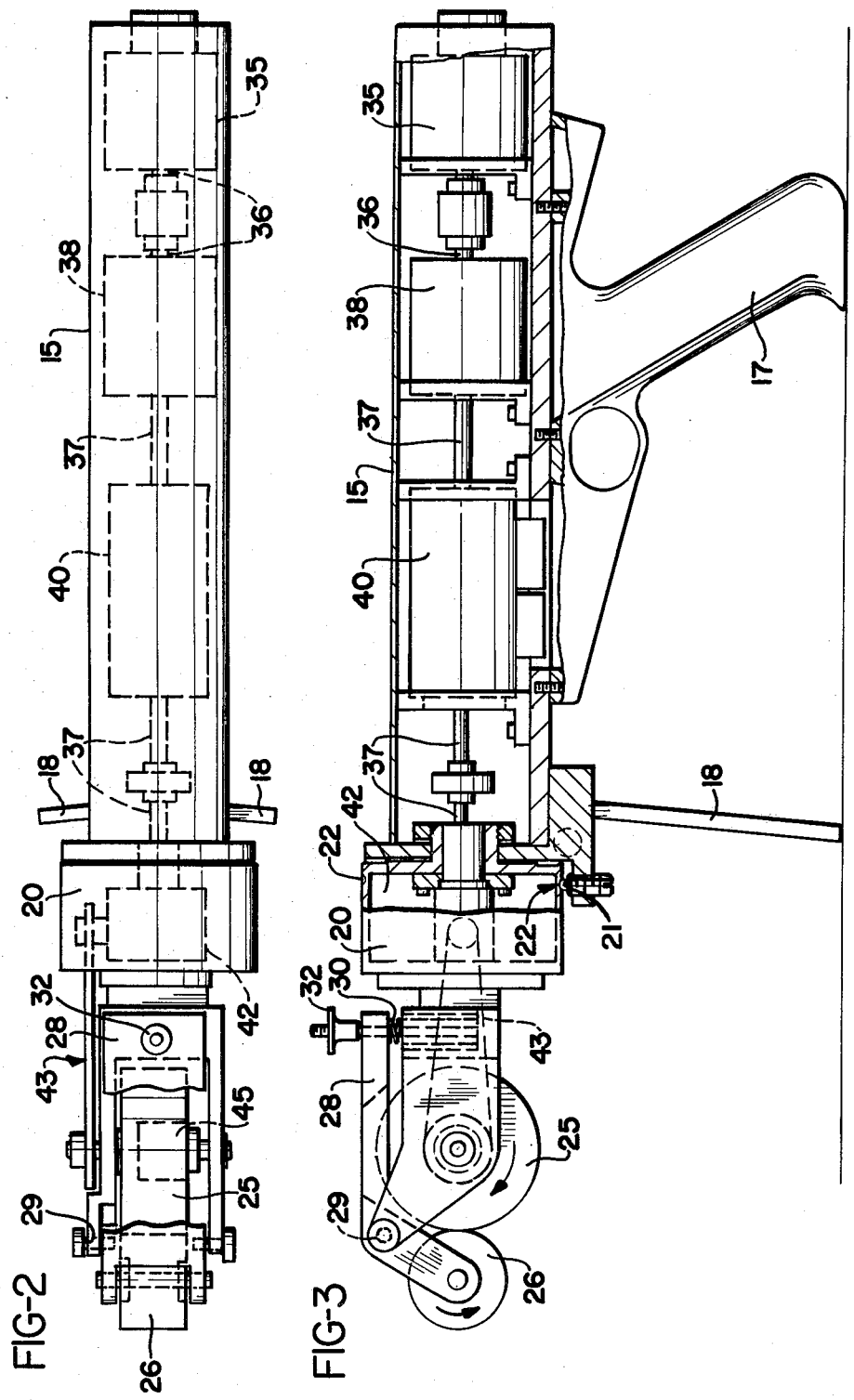

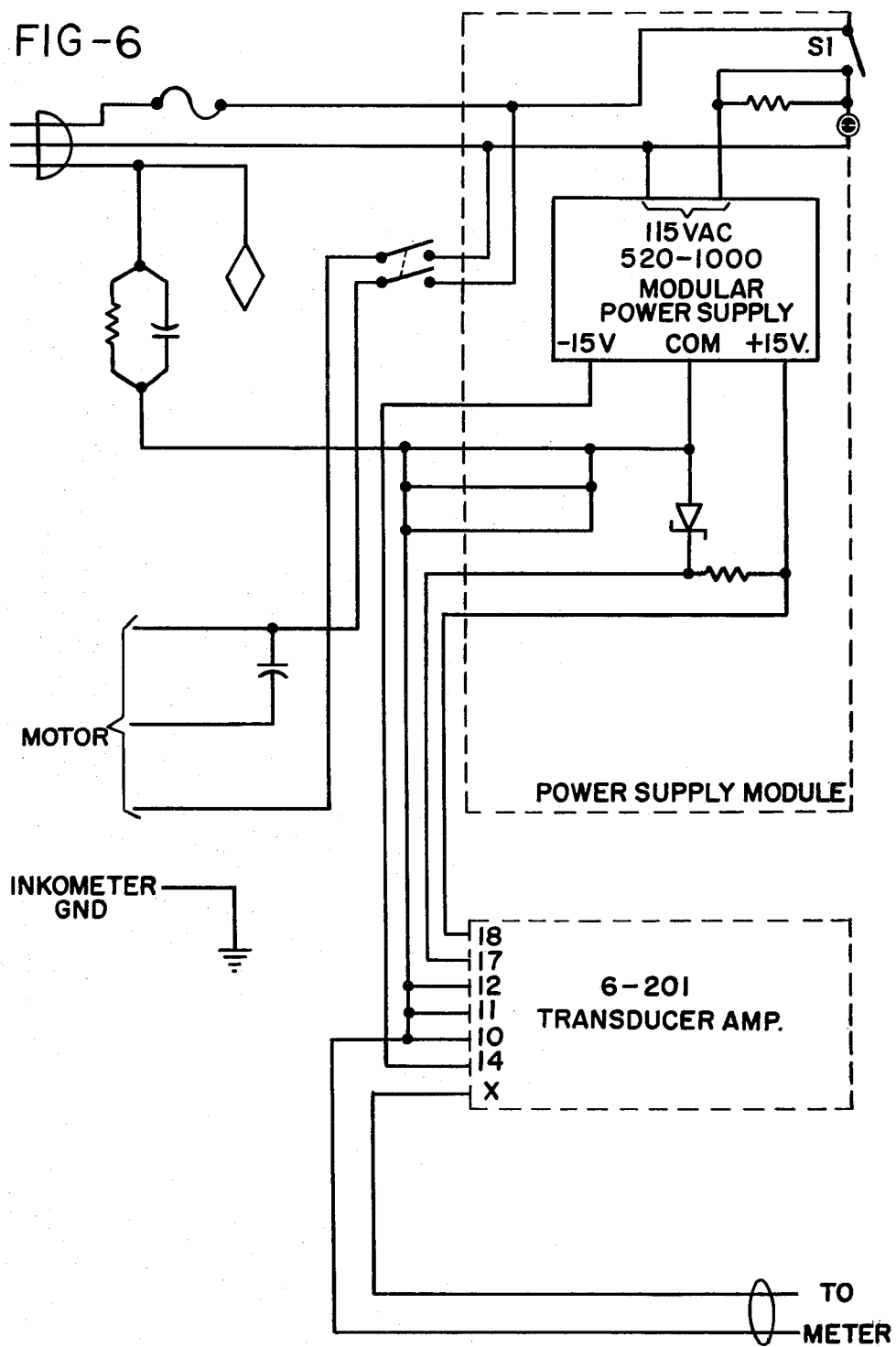

PORTABLE FLUID INK TACK TESTER

BACKGROUND OF THE INVENTION

The present invention relates to the testing of printing inks, and more particularly to a portable fluid ink tack tester for rapidly, conveniently and accurately measuring ink tack on printing presses at any time and any location.

Prior art fluid ink tack testers have for many years used the force necessary to split a film of ink as a suitable measure for the tack of the ink sample. Unfortunately, however, such devices are basically stationary in nature, in the sense that they are operated in a single location and the ink sample is brought to them. Not only is this inconvenient, but since the characteristics of many inks change rapidly when exposed to air, care and speed must be observed to obtain good results.

As a consequence, prior art devices have been proposed which are permanently mounted directly on the printing press to provide an automatic and continuous indication of the tack of the printing ink. Unfortunately, this requires that a discrete tack tester be provided for each inking couple in each printing tower. Not only does this multiply the cost several times over that of a single tester, but there can be physical problems in finding a suitable location and adequate space for these testers, where they are accessible to the machine operator.

A need therefore remains for an inexpensive, reliable, and rapidly operating portable instrument which can be conveniently carried to each inking unit, and will rapidly and accurately test the tack of the ink thereon before it can undergo significant change. Preferably, such a unit should be capable of being hand held and brought directly into contact with inked roll, and then immediately operated to give an indication of the tack of the ink.

SUMMARY OF THE INVENTION

Briefly, the present invention meets the above needs and purposes with a portable fluid ink tack tester having a manually portable frame which, in the preferred embodiment, provides a small, cylindrical package or configuration having a handle at one end, for manually holding the tester, and a roll extending outwardly from the other end, to expose the surface thereof for contacting an ink coated surface to receive an ink sample therefrom. The cylindrical frame defines a longitudinal axis therealong. The exposed roll is one of two rolls, both of which may have resilient surfaces, such as rubber, although in the preferred embodiment, one has a non-resilient surface, such as metal. The rolls are rotatably mounted on parallel axes on the frame in rolling contact with a predetermined pressure therebetween.

The ink tack tester also includes a motor for rotating the rolls. In the preferred embodiment, the motor is connected to one of the rolls for rotating it at a predetermined speed. Suitable means is then provided for measuring the force supplied to that roll by the motor and for displaying the measured force. In the preferred embodiment, the force is measured by a rotating strain guage mounted on the drive shaft which connects the motor to the driven roll.

In order to draw ink samples from printing presses having cylinders rotating either upwardly or downwardly, the present invention mounts the rolls of the ink tack tester so that their axes of rotation are transverse to the longitudinal axis of the frame, and so that they can be rotated about the axis of the frame for reversing the axes of the rolls. In this manner the rolls of the ink tack tester can be adjusted for rolling engagement with ink coated surfaces moving in either of two opposed directions. A one-way clutch couples the drive motor to the rolls to allow the rolls to rotate in the selected direction at a rate faster than that provided by the motor, so that the rolls may overrun the motor as the ink sample is being drawn from the printing press.

In the preferred embodiment, the rolls are carried on a mount which is rotatable about the longitudinal axis of the tester frame. The drive motor has an output shaft extending longitudinally along the frame coincidentally and coaxially with the longitudinal frame axis so that the rolls and mount can rotate about the axis of the drive shaft whenever the axis of the rolls is to be reversed. The motor is drivably connected by this drive shaft to the rolls through a right angle drive which is supported on the mount and moves with it, and the rolls, whenever the mount is rotated to reverse the roll axes.

A spring, operating through a lever arm and pivot, holds the extended roll against the other and supplies the aforementioned predetermined, constant pressure between them. With this pressure, the rolls may then be first operated while dry, and if necessary, a zero adjustment may be made for the measuring unit and circuitry. Standardized ink samples may then be applied to the rolls to enable the span (i.e., sensitivity) of the instrument to be calibrated, following which actual operational measurements of the tack of the ink or inks in question can be made.

It is therefore an object of the present invention to provide an improved portable fluid ink tack tester; an ink tack tester which is truly manually portable, and readily and easily usable in the field for measuring the tack of ink as it is being used on a printing press; which includes a manually portable frame having one of a pair of contacting parallel mounted rolls extending outwardly from one end of the frame to expose the surface of the extended roll for contacting an ink coated surface and receiving ink therefrom; which includes means for controllably rotating one of the rolls at a predetermined speed and for measuring the force supplied to the roll by the rotating means and displaying the measured force; and to accomplish the above objects and purposes in an economical, efficient, durable, reliable, and versatile configuration readily suited for rapidly and accurately measuring the tack of fluid inks in the widest possible variety of operating conditions.

Other objects and advantages of the invention will be apparent from the following description, the accompanying drawings and the appended claims.

BRIEF DESCRIPTION OF THE DRAWINGS

FIG. 2 is a partially broken away plan view of the tester minus the electronics and display package;

FIG. 3 is a partially broken-away side view of the FIG. 2 device;

FIG. 6 is an electrical schematic for the FIG. 1 tester;

DESCRIPTION OF THE PREFERRED EMBODIMENTS

Figure 1:
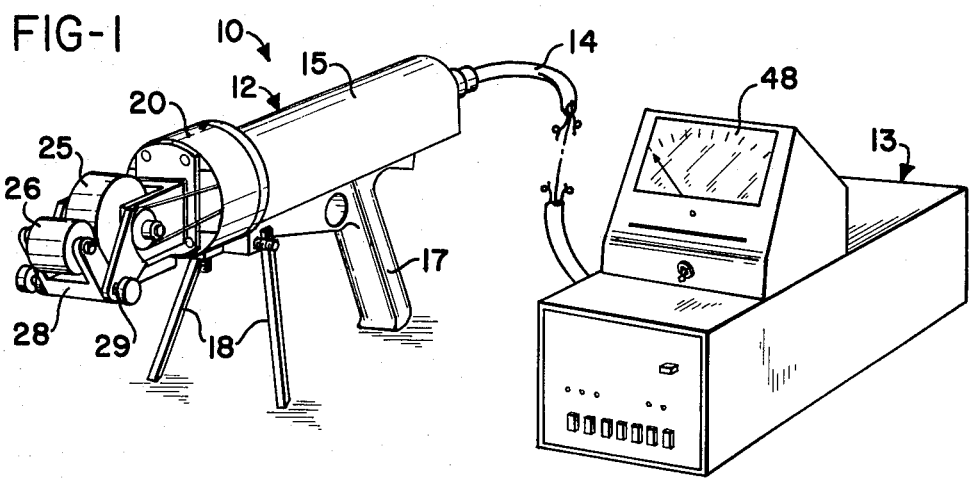
FIG. 1 is a perspective view of the preferred embodiment of the portable fluid ink tack tester according to the present invention.

With reference to the drawings, FIG. 1 illustrates the preferred embodiment of the portable fluid ink tack tester 10 of the present invention. Tester 10 includes a manually portable mechanical package 12 and a separate electronics and display package 13, connected by a cable 14. Package 12 has an elongated, generally cylindrical manually portable frame 15, the lengthwise center of which defines a longitudinal axis for the frame. A pistol grip 17 on one end makes it easy to hold and control the mechanical package 12, and retractable legs 18 at the other end cooperate with grip 17 to form a tripod base when the unit is not being held.

On the end of frame 15 opposite grip 17 is a mount 20 which is a part of the frame 15 and is rotatably mounted thereon for rotation about the longitudinal axis of the frame. In the preferred embodiment, it is rotatable through an angle of at least 180 degrees, and includes a ball plunger 21 which, in known fashion, retains mount 20 in two or more preselected positions corresponding to ball receiving recesses 22 in which ball 21 seats when positioned there. Mount 20, in turn, supports a roll 25 having a non-resilient surface, such as metal, and a roll 26 having a resilient surface, such as rubber. Rolls 25 and 26 are rotatably mounted on mount 20 with their surfaces in rolling contact and their axes of rotation parallel. Further, rolls 25 and 26 are positioned so that they extend outwardly from mount 20 and frame 15 along the longitudinal axis thereof. In the preferred embodiment, the smaller rubber roll 26 is extended the farthest to expose its surface for contacting an ink coated surface, such as an inking roll on a printing press, for receiving an ink sample therefrom.

To provide a predetermined pressure between the surfaces of rolls 25 and 26, roll 26 is mounted on a lever 28, which is pivoted at 29 to mount 20, and provides for moving roll 26 toward and away from roll 25. To keep the axes of rolls 25 and 26 parallel while applying this pressure evenly across the contact line or area, roll 26 may be pivotally mounted (not shown) on lever 28. The end of lever 28 opposite roll 26 is biased by a spring 30 to press the rolls together with a predetermined force or pressure therebetween. A knurled nut 32 can be tightened against lever 28 to overcome spring 30 and lift roll 26 off roll 25 when the tester 10 is not being used. This prevents flat spots from developing on the resilient surface of roll 26. When returned to use, nut 32 is withdrawn to a position spaced from and out of contact with lever 28, to assure restoration of the full predetermined pressure between the rolls.

Figure 5:
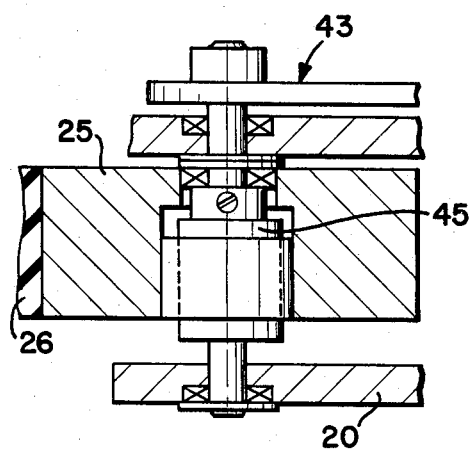
FIG. 5 is a fragmentary, enlarged cross-sectional view of portions of the FIG. 2 apparatus in the region including and surrounding the driven roll.

During calibration and testing, roll 25 is rotated at a predetermined speed by a drive motor 35 which has an output shaft 36 extending longitudinally along frame 15 coaxially with its longitudinal axis. Output shaft 36 is driveably connected therethrough to the driven roll 25 by suitable transmission and measuring devices, such as, for example, a drive train shaft 37, a speed reducer 38, a rotatable non-contacting torquemeter or strain guage 40, a right angle drive 42 in mount 20, and a drive belt and pulley arrangement 43. Within the metal roll 25 itself, as particularly shown in FIG. 5, is a one way clutch 45 which allows the rolls 25 and 26 to overrun the drive motor and drive train when roll 26 is in contact with a rapidly moving roll on a printing press.

Figure 4:
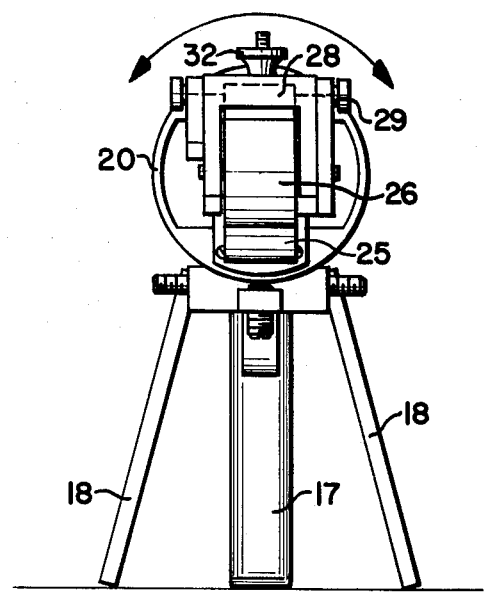
FIG. 4 is an end view of the FIG. 3 device as seen looking from left to right in FIG. 3.

The advantage of the reversible mount 20, which provides for reversing the axes of rolls 25 and 26, should now be clear. FIG. 1 shows them in one position; FIG. 3 in the reversed position. The FIG. 1 position would be employed for contacting a surface which is moving upwardly, while the FIG. 3 position (as shown by the arrows on the rolls) would be for a downwardly moving surface. The arrows in FIG. 4 illustrate rotation of mount 20 for reversing the axes of the rolls 25 and 26 to permit overrunning rotation in either direction.

The strain guage 40 measures the torque developed on the drive train shaft 37 as it carries the torque (force times the moment arm) developed by motor 35 to the rubber rolls 25 and 26. Since the torque on the shaft and the ink film splitting force it represents are directly related in known fashion, measuring the torque will provide a direct proportional indication thereof. Any suitable method for measuring and displaying the output developed by motor 35 and transmitted to the rolls may therefore be employed. The in-line non-contacting torquemeter or strain guage 40 has been found particularly effective. It provides high accuracy and repeatability, and is easy and convenient to operate. In the preferred embodiment, a model MCRT 3-08T torquemeter manufactured by S. Himmelstein & Co., Elk Grove, Ill., is used, with only slight modification to the electronic circuitry thereof, as illustrated in FIG. 6.

In use, nut 32 is first withdrawn to place rolls 25 and 26 in contact. While the rolls are still dry, motor 35 is energized to rotate the rolls, and meter 48 on the electronic package 13 is zeroed, if necessary. Several known samples of ink are then run on the rolls, and the span (i.e., sensitivity or amplification) of the instrument is adjusted so that the indications on meter 48 correspond with the tack values of these known samples. Tests have shown that subsequent samples taken on printing presses will be accurately tested. In face, tester 10 is so stable that no further calibration is required for the balance of the day. Even after the tester is cleaned and stored, it is usually within one unit (approximately 4%) of proper calibration when again put in service.

Figure 7:
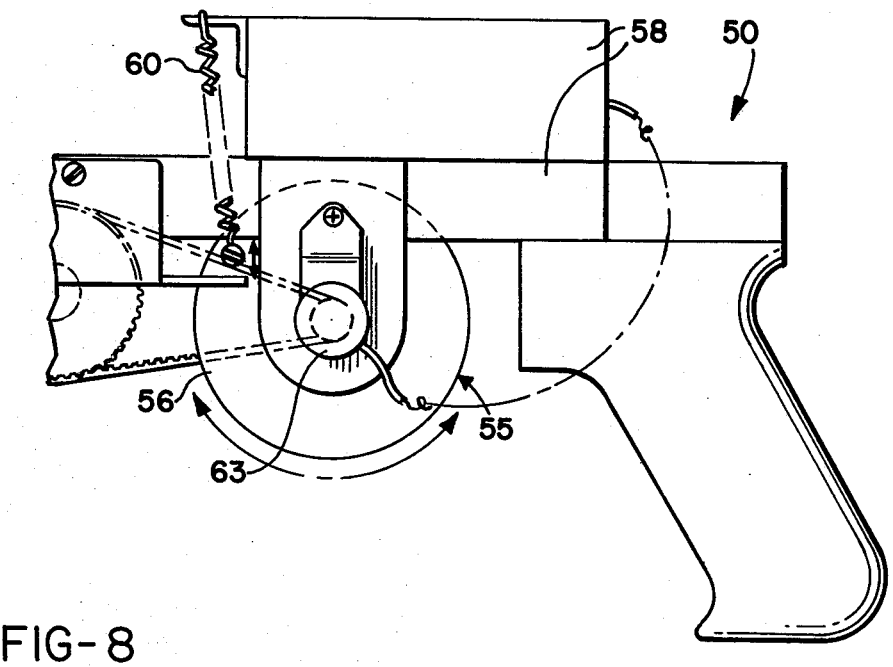
FIG. 7 is a fragmentary side view illustrating a modification of the FIG. 1 tester.
Figure 8:
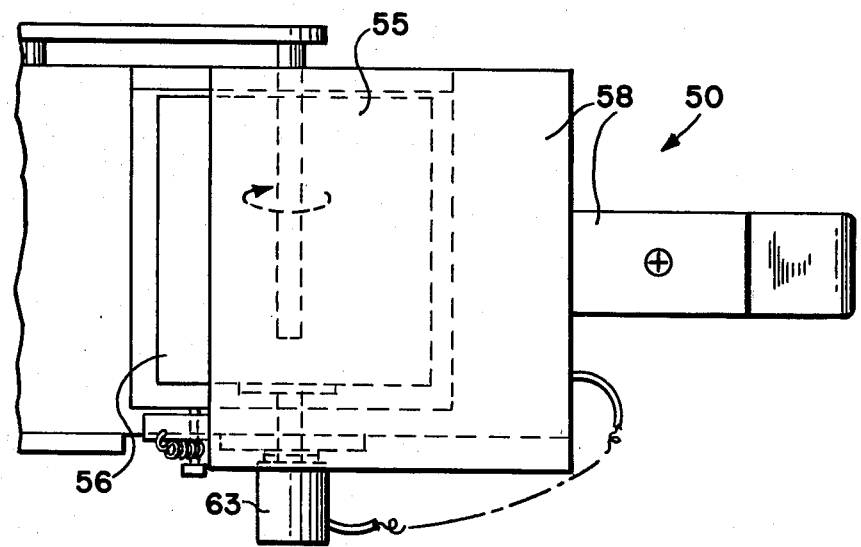
FIG. 8 is a top view of the FIG. 7 modification.

FIGS. 7 and 8 illustrate an alternate tester embodiment 50 which is similar to tester 10. The principle difference is in the way the torque developed by its motor 55 is measured. The motor housing 56 is rotatably mounted on the tester frame 58. A spring 60 is tensioned between one end of frame 58 and motor housing 56 so that, as the motor housing rotates under the reaction torque of its output, spring 60 stretches until it balances the torque and transmits it to the frame 58. The rotation of the motor housing 56 is thus proportional to the torque developed by motor 55, and may be detected and displayed to indicate the tack of the ink. A mechanical pointer may be used, or as illustrated, a rheostat 63 may be attached to the motor housing 56 to provide an output for a suitable electronic detecting and indicating circuit (not shown).

As may be seen, therefore, the present invention has numerous advantages. It is compact, light weight, and can easily be carried to the location where the ink is actually being used. Roll 26 is well exposed at the extreme front end for easily engaging the surface from which the ink sample is to be drawn. Mount 20 provides for reversing the axes of the rolls 25 and 26 so that, with the aid of the overrunning or one-way clutch, they can turn freely in the direction necessary for receiving the ink sample. The rotating, in-line strain guage 40 provides a sensitive and accurate indication of the torque which is developed by motor 35, without requiring mechanical coupling between the drive train and the electronics and display package 13. The electrical output signal (which is an a.c. signal) is brought out through rotary transformer windings to the analyzer circuit through cable 14. No slip rings are needed. After the tester has been initially calibrated, the strain guage 40 and its associated circuitry then measures the additional or differential torque developed on the drive shaft when ink is added to the surfaces to the two rotating rolls. This additional torque is directly related and proportional to the force necessary to split the film of ink on the rolls 25 and 26, there- by providing a direct indication of the tack of the ink sample thereon. Alternatively, other means for measuring the differential torque which is developed may be utilized, such as illustrated in tester 50 (FIGS. 7 and 8).

While the forms of apparatus herein described constitute preferred embodiments of the invention, it is to be understood that the invention is not limited to these precise forms of apparatus, and that changes may be made therein without departing from the scope of the invention.

What is claimed is:

1. A portable fluid ink tack tester comprising:
   (a) a manually portable frame having a longitudinal axis,
   (b) first and second rolls,
   (c) mounting means rotatably mounting said rolls on parallel axes of rotation on said frame and in rolling contact, with a predetermined pressure therebetween, and positioned with at least one of said rolls supported and extending outwardly from said frame to expose the surface thereof for contacting an ink coated surface and receiving an ink sample therefrom,
   (d) rotating means including a drive shaft for controllably rotating said first roll at a predetermined speed,
   (e) a rotating strain gauge mounted on said drive shaft for measuring the force supplied to said first roll by said rotating means, and
   (f) means for displaying said measured force.

2. The apparatus of claim 1, wherein said rotating means includes a drive motor having a housing rotatably supported on said frame, and said strain guage is coupled between said motor housing and said frame to measure the torque developed by said motor and to transmit said torque to said frame.

3. A portable fluid ink tack tester comprising:
   (a) a manually portable frame having a longitudinal axis,
   (b) first and second rolls, the axes of which are transverse to the longitudinal axis of said frame,
   (c) mounting means rotatably mounting said rolls on parallel axes of rotation on said frame and in rolling contact, with a predetermined pressure therebetween, and positioned with at least one of said rolls supported and extending outwardly from said frame to expose the surface thereof for contacting an ink coated surface and receiving an ink sample therefrom,
   said mounting means including means for reversing the axes of said rolls to provide for rolling engagement with ink coated surfaces moving in either of two opposed directions,
   (d) rotating means for controllably rotating said first roll at a predetermined speed and including a drive motor mounted on said frame and having an output shaft extending longitudinal along said frame, a right angle drive shaft connected to said motor output shaft, and a one-way clutch coupling said right angle drive shaft to said first roll to provide for rotating said rolls in one direction at a rate faster than provided by said motor,
   (e) measuring means for measuring the force supplied to said first roll by said rotating means, and
   (f) means for displaying said measured force.

4. A portable fluid ink tack tester comprising:
   (a) a manually portable frame having a longitudinal axis,
   (b) first and second rolls, said first roll having a metallic surface and the other a rubber surface,
   (c) mounting means rotatably mounting said rolls on parallel axes of rotation on said frame and in rolling contact, with a predetermined pressure therebetween, and positioned with at least one of said rolls supported and extending outwardly from said frame to expose the surface thereof for contacting an ink coated surface and receiving an ink sample therefrom,
   (d) said mounting means mounting the axes of said rolls transversely to the longitudinal axis of said frame and including means for reversing the axes of said rolls by rotating them about the longitudinal axis of said frame to provide for rolling engagement with ink coated surfaces moving in either of two opposed directions,
   (e) rotating means connected for controllably rotating said first roll at a predetermined speed, and including a drive motor mounted on said frame and having an output shaft extending longitudinally along said frame, a drive shaft connected to said motor output shaft and passing into said mounting means coaxially with the longitudinal axis of said frame, a right angle drive supported on said mounting means and driveably connected to said drive shaft, and a one-way clutch driveably coupling said right angle drive to said first roll to provide for rotating said rolls in one direction at a rate faster than that provided by said motor,
   (f) a rotating strain gauge mounted on said drive shaft for measuring the force supplied to said first roll by said rotating means, and
   (g) means for displaying said measured force.

* * * * *